(12) United States Patent
Heid

(10) Patent No.: US 9,606,026 B2
(45) Date of Patent: Mar. 28, 2017

(54) CUTTING STROKE ADJUSTMENT OF A ROTARY MICROTOME

(75) Inventor: Hans Ludwid Heid, Bammental (DE)

(73) Assignee: Hans Heid, Bammental (DE)

( * ) Notice: Subject to any disclaimer, the term of this patent is extended or adjusted under 35 U.S.C. 154(b) by 217 days.

(21) Appl. No.: 13/825,326

(22) PCT Filed: Sep. 21, 2011

(86) PCT No.: PCT/DE2011/001771
§ 371 (c)(1),
(2), (4) Date: Mar. 21, 2013

(87) PCT Pub. No.: WO2012/041284
PCT Pub. Date: Apr. 5, 2012

(65) Prior Publication Data
US 2013/0186248 A1    Jul. 25, 2013

(30) Foreign Application Priority Data

Sep. 24, 2010  (DE) ................ 10 2010 046 498

(51) Int. Cl.
*B26D 5/00* (2006.01)
*G01N 1/06* (2006.01)

(52) U.S. Cl.
CPC ......... *G01N 1/06* (2013.01); *G01N 2001/065* (2013.01); *Y10T 83/87* (2015.04)

(58) Field of Classification Search
CPC .................................. G01N 1/06; Y10T 83/87
USPC ............ 83/915.5, 530, 703, 728, 403.1, 856
See application file for complete search history.

(56) References Cited

U.S. PATENT DOCUMENTS

| 3,785,234 | A | * | 1/1974 | Sitte ............................... 83/414 |
| 4,479,402 | A | * | 10/1984 | Reichel et al. ................. 74/625 |
| 4,495,844 | A | * | 1/1985 | Jackson et al. ................. 83/715 |
| 4,594,929 | A | * | 6/1986 | Behme et al. .................. 83/715 |
| 4,702,464 | A | * | 10/1987 | Bauer et al. .................... 269/55 |

(Continued)

FOREIGN PATENT DOCUMENTS

| DE | 000002253628 A | 6/1973 |
| DE | 3806269 C1 | 4/1989 |

(Continued)

*Primary Examiner* — Omar Flores Sanchez

(57) ABSTRACT

A rotary microtome (1) for producing thin sections for histology is used for specimens (6) of different sizes. To maintain optimized cutting conditions, an adaptation to different specimen sizes is required without incurring disadvantages in terms of operation. An adjustment possibility is provided for the length of the vertical cutting movement (10). However, the moment that is generated by the vertical carriage (7) and that acts on the drive shaft (12) then changes. To maintain balanced moments of the drive movement, the counterweight has to be accordingly adapted by an adjustment weight (31). For this purpose, means are provided which, in an ergonomic and effective manner, permit the adjustment of the cutting stroke and also the necessary adaptation of the counterweights in one operation step. The rotary microtome according to the invention is suitable in particular in a histological routine in which mixed specimens are present in standard cassettes and also in macrocassettes and in which, therefore, a rapid change of the cutting stroke length is desired along with good balance of the drive movement.

18 Claims, 12 Drawing Sheets

(56) References Cited

U.S. PATENT DOCUMENTS

| | | | |
|---|---|---|---|
| 5,881,626 A * | 3/1999 | Kiene et al. | 83/707 |
| 6,209,437 B1 * | 4/2001 | Izvoztchikov et al. | 83/707 |
| 6,253,653 B1 * | 7/2001 | Walter et al. | 83/703 |
| 6,267,050 B1 * | 7/2001 | Brewer | 100/257 |
| 8,113,099 B2 * | 2/2012 | Lihl et al. | 83/603 |
| 8,347,769 B2 * | 1/2013 | Walter | 83/13 |
| 8,353,232 B2 * | 1/2013 | Walter et al. | 83/13 |
| 8,869,666 B2 * | 10/2014 | Yang et al. | 83/360 |
| 2001/0054345 A1 * | 12/2001 | Krauss et al. | 83/703 |
| 2010/0058913 A1 * | 3/2010 | Walter | 83/648 |

FOREIGN PATENT DOCUMENTS

| | | |
|---|---|---|
| DE | 000004339071 A1 | 5/1995 |
| DE | 102008016165 A1 | 10/2009 |
| DE | 102008031137 A1 | 1/2010 |

* cited by examiner

--Prior Art--

CUTTING STROKE ADJUSTMENT OF A ROTARY MICROTOME

CROSS-REFERENCE TO RELATED APPLICATION

This application claims the priority of the PCT application PCT/DE2011/001771 based on German application DE 10 2010 046 498 having a priority date of Sep. 24, 2010, the entire content of which is herewith incorporated by reference.

BACKGROUND OF THE INVENTION

Technical Field

Microtomes are used to cut thin sections, usually of organic tissue, for microscopic examination. This is a common process in histology labs and pathology. There are several types of microtomes. Commonly used are sledge microtomes and rotary microtomes. Usually the cutting stroke of a microtome is of fixed length.

A generic rotary microtome is being described in DE 3806269 C1 for example. The invention relates to a cutting stroke adjustment of such a rotary microtome for improved working conditions in histology labs.

Background Art

Rotary microtomes are characterized by a vertical cutting movement of the specimen holding device with the thereto attached specimen to be thin cut and a horizontal feed movement between cutting knife and specimen surface of the amount of the preset sectioning thickness. Depending on the type of the respective rotary microtome the horizontal feed can be arranged either by moving the knife or the specimen.

The vertical cutting movement of the specimen holding device, as part of a vertically moved carriage of a rotary microtome, is performed by a circular driving movement of a driving shaft, having at one end a crank arm with a thereto connected crank pin. That crank pin being freely rotatable engaged in a link piece guided in a motion link path thus resulting in a linear vertical movement of said vertical carriage.

Alternatively a corresponding crank pin can act together with other forms of horizontal guidances as described for example in DE 000004339071A1.

The circular driving movement can either take place manually by a handwheel with a handle or also be performed motorized thru a pulley connected to the driving shaft. When having a constant angular velocity of the driving circular movement the velocity of the resulting vertical movement has a sinus component.

The stroke length of the linear vertical movement of the specimen holding device with the thereto attached specimen corresponds to the diameter of the circle being described from the crank pin center on its travel around the center of the driving shaft.

The size of the cutting stroke length and thus the size of the circle diameter is for logical reasons elected to be in the range of the length of the specimen to be cut or respectively with some reserve distance in order to enable a problem free cutting into the specimen.

However, with a variation of tasks regarding the size of specimens it turns out that it is of disadvantage to have a cutting stroke length which is a fixed length by design. Therefore it was disclosed in the earlier publication DE000002253628 A to have a cutting stroke length adjustment to accommodate the different requirements from specimen sizes in routine histology on one side and in ultramicrotomy on the other side in order to cover both tasks with one type of apparatus.

This however did never gain acceptance.

But in the last years an increased demand occurred in the main field of usage of rotary microtomes, namely in routine histology, to cut besides the very often used specimen sizes of typically up to 30 mm length which are incorporated in so called standard cassettes also other specimen which are incorporated in so called macro-cassettes within the same laboratory and with the same microtomes. These macro-cassettes incorporate specimen sizes of around 70 mm length. Therefore in the first instance a trend started to increase the fixed cutting stroke length of most of the commercially available rotary microtomes from so far around 60-65 mm to stroke length of 70-75 mm without offering in the first place the already known possibility of a variable cutting stroke length of the apparatus.

This has rather negative consequences for the sectioning quality and ergonomy as well as for the efficiency of the working process, because on a worldwide basis more than 90% of routinely arising specimen have specimen sizes less than 30 mm. Microtomes with fixed stroke length of 60-65 mm were already of great disadvantage for the majority of specimen sizes, but this situation became worse with the introduction of the macro-cassette and the adaptation of the fixed stroke length to the maximum size.

The sectioning quality, namely to avoid compression of the sections and to avoid so called chatter on the sections produced, is greatly dependant from the cutting speed. Therefore it is a goal to maintain the lowest possible cutting speed with having a high specimen throughput and a high sectioning sequence. This means for rotary microtomes absolutely to provide a short cutting stroke length for the majority of specimen. In addition it is in view of ergonomy and work place efficiency important to avoid unnecessary phases of idle movement with the type of specimens used most. To offer nevertheless universal apparatus the demand for a variable cutting stroke length raises again.

In DE 102008016165 A1 this requirement is regarded to a certain extent.

However, the microtome described there has only motorized function and there are no means for a direct mechanical coupling of a handwheel with handle and the resulting sectioning process.

This is of disadvantage, because it is known that the user does not want to give up the manual operation in the phase of first cuts into the specimen and also for delicate specimen. Therefore a backlash-free mechanical coupling is of importance for an adequate sensoric feedback to the manual operating user and of unvaluable worth in case of difficult specimen material with enhanced sectioning requirements.

Hence rotary microtomes with mechanically coupled handwheels are preferred even when they are operated motorized optionally.

In DE 102008031137 A1 a cutting stroke adjustment for a rotary microtome is described. There is also mentioned the difficulty with rotary microtomes which arises from necessary compensating weights in case of a variable cutting stroke adjustment.

Commonly, rotary microtomes have a compensation mass for compensation of vertically movable mass which generates together with the crank arm of the crank pin a moment of force. The compensation mass being connected to the drive shaft generates with its distance of the center of mass to the drive axle a countermoment of force of same amount but with 180° phase shift. From that results the desired and necessary balance of the driving movement. With a variable adjustable cutting stroke it is therefore in any case necessary to have a corresponding alignment of the effect of the compensation mass. This can be achieved either by changing the mass itself or by changing the effective lever arm of force.

In DE 102008031137 A1 is a cutting stroke adjustment described as well as an accordingly necessary compensation mass adjustment. Both adjustments being conducted from outside with tools and in sequence. For adjusting the cutting stroke and the compensation mass a locking mechanism is in place in order to have access to the positions of the adjusting means thru openings of the microtome housing.

The means described in DE 102008031137 A1 meet admittedly the basic requirements for an adjustment of the cutting stroke matching the specimen sizes in use, however they are cumbersome and time-consuming in their execution.

This is of gross disadvantage in the routine operation in a histology laboratory, particularly if several times a day there is a need to change from regularly used small specimens to large specimens and back.

BRIEF SUMMARY OF THE INVENTION

It is an object of this invention to create a rotary microtome as described with a cutting stroke adjustment, which enables a clearly improved handling of the cutting stroke adjustment and as well achieves as a significant attribute a coupled adjustment of the effective compensation mass together in one operation step, without use of tools and without the need of locking of the drive parts.

This object is achieved with a rotary microtome of the described type with the implementation of means which enable the adjustment of a steplessly electable cutting stroke length, whereby further means which are in a fixed relation cause a steplessly adjustment of a compensation weight and whereby means are provided to enable an operational step with operational means for the cutting stroke adjustment and at same time adjustment of a compensation weight and where these operational means are easily accessible from the outside of the microtome.

The elected means are designed in a way, that for operating the adjustment of the cutting stroke there is no need for the use of tools nor there is a need for a locking or fixation of the driving mechanics and the cutting stroke adjustment with synchronous adjustment of the compensation weight is carried out in a single operational step.

This can be achieved by operating a single mechanically acting control element or alternatively by actuating electromotorized or electromagnetic means thru a respective control unit which may be part of the main control unit of the microtome.

This has the advantage that the user can expeditiously and ergonomically adjust the microtome for the given situation of different specimen sizes in order to obtain, with optimized operating parameters, an improved sectioning quality of the specimen sections.

An advantageous embodiment of the setting mechanics of the cutting stroke adjustment is to arrange the crank pin, which effects the transformation of the rotational drive movement into a linear cutting movement, steplessly adjustable in its distance to the driving axis via a crank pin adjustment unit.

Thereby a translational or rotatory adjustment movement is carried out by a control element which is situated at the outside of the microtome and which is ergonomically accessible to the operator. Said adjustment movement is acting on the shifting of the distance between crank pin centerline and driving axis thru transferring adjustment means, which are located inside of the lateral surface of the driving shaft and are driving the crank pin adjustment unit in a respective way.

Simultaneously further transferring adjustment means, which are also located inside the lateral surface of the driving shaft and which are also driven by the same translational or rotatory adjustment movement of the control element, act on a weight adjustment unit in a way, that an adjustment weight, which is a partial weight of the total compensation weight is shifted radial to the driving axis and in opposite direction to the crank pin with the condition that $M_V=M_A$ is true for any rotation angle of the driving movement. Thereby the weight adjustment unit is engaged thru an opening in the lateral surface of the driving shaft with one of the said transferring adjustment means located inside the lateral surface of the driving shaft.

There is $M_V$ the moment of force $$m_V*g*r_V*\sin \alpha, \text{ with}$$

$m_V$=vertically moved mass, carrying out the cutting stroke,
g=gravitational acceleration
$r_V$=radius of circle of crank pin travel=half of a stroke length,
$\alpha$=rotation angle of driving movement (0°-360°),
and $M_A$ the moment of force $$m_A*g*r_A*\sin(\alpha+180°), \text{ with}$$

$m_A$=compensation mass,
$r_A$=distance of center of compensation mass to driving axis.

In case of a splitting of the compensation weight, as described herein, in a fixed compensation weight and an adjustable weight it is:

$$M_A=m_{AF}*g*r_{AF}*\sin(\alpha+180°)+m_{AV}*g*r_{AV}*\sin(\alpha+180°) \text{ with,}$$

$m_{AF}$=fixed compensation mass
$r_{AF}$=distance of the center of mass of the fixed compensation mass to the driving axis
$m_{AV}$=adjustable compensation mass
$r_{AV}$=distance of the center of mass of the adjustable compensation mass to the driving axis.

With $M_V=M_A$ it is:

$$m_V*g*r_V*\sin \alpha = m_{AF}*g*r_{AF}*\sin(\alpha+180°)+m_{AV}*g*r_{AV}*\sin(\alpha+180°) \text{ and therefore}$$

$$m_V*g*r_V*\sin \alpha = m_{AF}*g*r_{AF}*\sin(-\alpha)+m_{AV}*g*r_{AV}*\sin(-\alpha)$$

$$m_V*g*r_V*\sin \alpha = -m_{AF}*g*r_{AF}*\sin \alpha - m_{AV}*g*r_{AV}*\sin \alpha$$

$$m_V*g*r_V*\sin \alpha = -g*\sin \alpha(m_{AF}*r_{AF}+m_{AV}*r_{AV})$$

$$m_V*r_V = -(m_{AF}*r_{AF}+m_{AV}*r_{AV})$$

Thereby the variation of the moment of force $M_V$ is practically only in the range between $r_V$min and $r_V$max, e.g. corresponding to the elected minimum stroke length and the maximum stroke length.

Regarding the specimen sizes outlined above $r_V$min will be typically elected in the range of ½ $r_V$max. However naturally any other ratio<1 is possible.

For the corresponding compensation moment of force, which is preferably composed by adding a fixed compensation mass and an adjustable compensation mass, there is a wide field of choice in splitting the ratio of fixed mass to adjustable mass. A notably preferred splitting is in a way, that the moment of force that is generated by the fixed compensation mass represents about the middle value of the necessary maximum moment of force and minimum moment of force and therefore the remaining adjustable compensation moment of force will need to adopt as well positive as also negative compensation moments of force to fulfill the task.

This means, that the center of mass of the adjustable compensation mass can be located on the same side as the fixed mass in relation to the driving axis (positive compensation moments of force), as well as on the opposite side (negative compensation moments of force). This is advantageous, because the physically available space around the driving axle or respectively on the handwheel corpus can be used on all sides.

Therefore a maximum adjustment track within a selected constructive frame is given in favor of a best resolution of adjustment.

Moreover the adjustment operation can be carried out completely independent of the actual orientation and position regarding the angular situation of the driving shaft and a with it connected handwheel or connected pully. Instead of a mechanically acting control element it is certainly also possible to use for example gear motors or electric pushing or pulling solenoids which can be operated by a respective control unit.

An embodiment for above-mentioned translational transferring adjustment means is constructed in a way, that a pushing rod is supported to be axially shiftable inside the driving shaft which is constructed as hollow shaft. Thereby a lever mechanics which is in connection with the pushing rod and which is on the operational side outside of the handwheel is providing the amount of shifting. On the opposite side of the pushing rod a 90° conversion, which is a further part of the said transferring adjustment means, is driving a crank pin adjustment unit. This can be effected for example in having at the end of the pushing rod a toothed rod connected acting in the shifting direction and that a related pinion is driving a spindle acting on an adjustment sledge of the crank pin adjustment unit.

Additionally there is another transferring adjustment means on the middle part of the pushing rod, which is acting thru an opening in the lateral surface of the driving shaft and which is in contact with a coupled driving means driving the weight adjustment unit in a 90° angle in a way, that with operating the control element there is simultaneously a cutting stroke adjustment and as well a suitable weight adjustment of the variable compensation weight taking in account also the fixed compensation weight. This has the consequence that the moment of force which is created by the vertically moving mass on the crank pin is compensated for any angle of the driving movement.

The transferring adjustment means which is acting on the weight adjustment can be also a toothed rod which is oriented in the direction of the pushing rod and which is connected thereto for example. The further needed coupled driving means which is acting thru an opening of the lateral surface of the driving shaft then can be for example a pinion matching to the said toothed rod. Said pinion can for example drive an adjustment spindle of the weight adjustment unit.

A control element for a translational adjustment in direction of the axis of the driving axle of the microtome can be represented by a simple handle-like extension of the pushing rod on the operating side. An unintentional adjustment move is prevented if the driven spindles of the crank pin adjustment unit or the weight adjustment unit have self-retention.

In a further embodiment the control element can be represented by a lever mechanics, which, when operated, results accordingly to said translational adjustment in the axial direction of the driving axle.

The positioning of said pushing rod inside the hollow driving shaft and therefore also the positioning of the other transferring adjustment means connected to the pushing rod can be concentric or also excentric and can be selected depending on the constructive elaboration and requirements.

An embodiment for rotary transferring adjustment means as above-mentioned is constructed in a way that an adjustment shaft is supported in a bearing concentrically inside the driving shaft which is constructed as hollow shaft, whereby at the operational end of the driving shaft, outside of the handwheel or a pulley respectively, a dial wheel is connected to the adjustment wheel and serving as control element.

At the opposite side of the adjustment shaft a 90° redirecting means which is a further part of the transferring adjustment means is driving a crank pin adjustment unit.

This can be achieved for example in a way, that at the end of the adjustment shaft a driving bevel gear wheel is connected which is meshing with a down force bevel gear wheel which is driving a spindle which is acting on an adjustment sledge of the crank pin adjustment unit.

Additionally there is another transferring adjustment means on the middle part of the adjustment shaft, which is acting thru an opening in the lateral surface of the driving shaft and which is in contact with a coupled driving means driving the weight adjustment unit in a 90° angle in a way, that with operating the control element there is simultaneously a cutting stroke adjustment and as well a suitable weight adjustment of the variable compensation weight taking in account also the fixed compensation weight. This has the consequence that the moment of force which is created by the vertically moving mass on the crank pin is compensated for any angle of the driving movement. For example, the transferring adjustment means acting on the weight adjustment can be a worm gear connected to the adjustment shaft. The further coupling driving means, which is meshing thru the described opening in the lateral surface of the driving shaft, then can be for example a worm wheel matching to the said worm gear, the worm wheel being part of the weight adjustment unit and that way driving that weight adjustment unit.

A further embodiment for rotary transferring adjustment means as above-mentioned can be in a way to simply combine the above-mentioned realization with a different form of weight adjustment.

Thereby the transferring adjustment means which is acting on the weight adjustment can be a pinion which is sitting on the adjustment shaft for example.

The further coupling driving means, which is meshing thru the described opening in the lateral surface of the driving shaft, then can be for example a toothed rod which is matching to the said pinion, the toothed rod being part of the weight adjustment unit and shifting the adjustment weight.

The dial wheel which is acting as control element is fixed in place at the respective control position against an unintentional adjustment move for both embodiments of the rotary transferring adjustment means. This is achieved, if the driven spindle of the crank pin adjustment unit has a self-retention by design.

Furthermore, the dial wheel which is acting as control element can be substituted by a gear motor which is installed inside the driving shaft which is realized as hollow shaft. The gear motor then is connected to a control unit and a respective operational unit and its electrical supply is established via sliding contacts at the driving shaft or the handwheel.

BRIEF DESCRIPTION OF THE SEVERAL VIEWS OF THE DRAWINGS

The invention will be explained in more detail by embodiments illustrated in drawings. For components which are connected to each other the representation of the respective fasteners was spared for reasons of clarity. Further alternative embodiments of this invention are naturally achievable as well.

The drawings illustrate in

A perspective view of a known rotary microtome corresponding to the state of the art

FIG. 2

A perspective view of a known vertical carriage corresponding to the state of the art

FIG. 3

A perspective view of a known driving unit corresponding to the state of the art

FIG. 4

A schematic depiction of a known rotary microtome with a stroke adjustment corresponding to the state of the art

FIG. 5

Front view of a crank pin adjustment unit according to the invention

FIG. 6

A perspective view of the crank pin adjustment unit with adjustment shaft and dial wheel

FIG. 7

A perspective view of a driving unit with incorporated crank pin adjustment unit

FIG. 8

A further perspective view of a driving unit with incorporated crank pin adjustment unit and visible dial wheel

FIG. 9

A perspective view of a weight adjustment unit on a handwheel according to the invention

FIG. 9a

Figure 9:
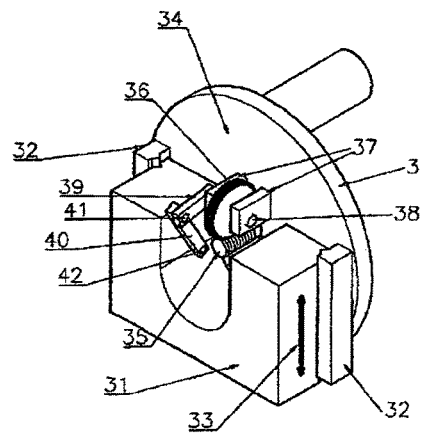

A top view of the weight adjustment unit on a handwheel shown in FIG. 9

FIG. 10

A perspective view of a coupled crank pin adjustment unit with weight adjustment unit according to the invention

FIG. 10a

A perspective view of a coupled crank pin adjustment unit with a weight adjustment unit on a modified driving shaft with directly connected guidances

FIG. 10b

Figure 10:
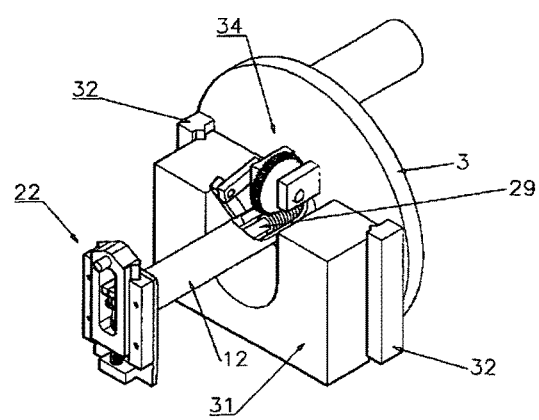
Figure 10A:
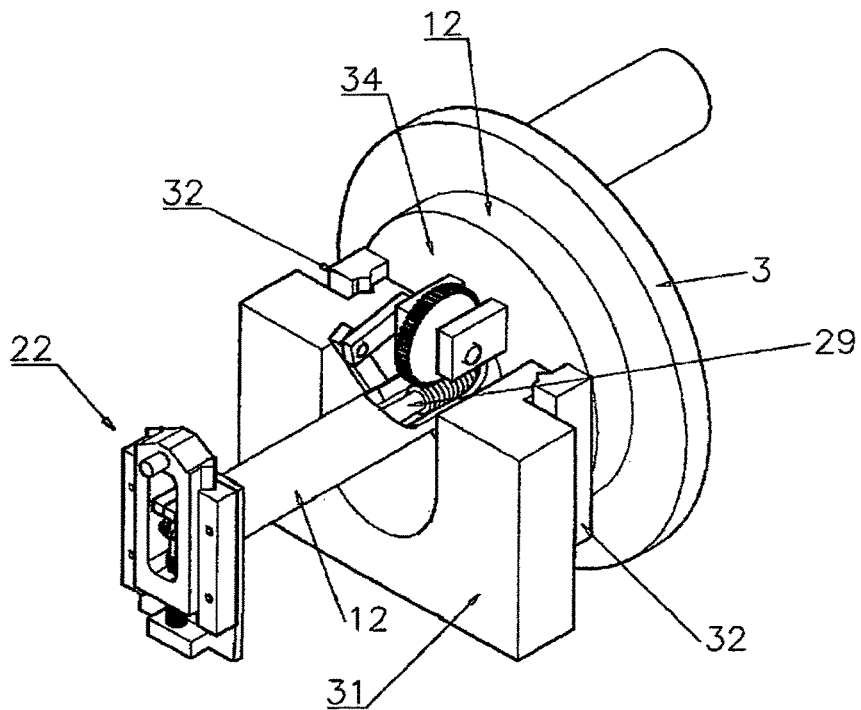

A cross section of the arrangement in FIG. 10a with the modified driving shaft

FIG. 11

A perspective view of a further example of a weight adjustment unit according to the invention

FIG. 12

A perspective view of a further example of a coupled crank pin adjustment unit with a weight adjustment unit

FIG. 13

A perspective view of a complete driving unit with coupled crank pin adjustment unit and weight adjustment unit and an additional fixed compensation weight according to the invention

FIG. 14

A perspective view of an embodiment on a rotary microtome according to the invention

FIG. 15

A schematic depiction of a rotary microtome with a coupled crank pin adjustment unit and weight adjustment unit according to the invention

FIG. 16

A schematic depiction of a rotary microtome with a coupled crank pin adjustment unit and weight adjustment unit and an optional pulley for a motorized cutting drive as well as a gear motor to drive the transferring adjustment means according to the invention

DETAILED DESCRIPTION OF THE INVENTION

Figure 1:
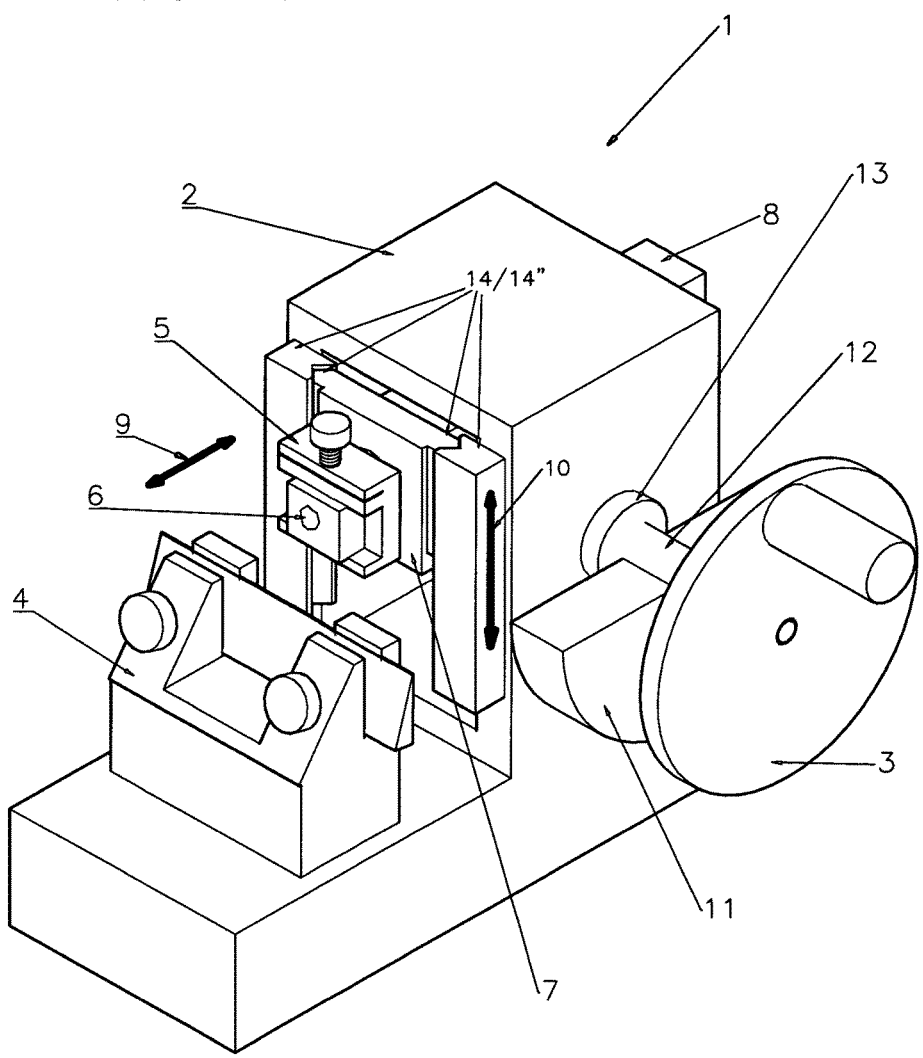
FIG. 1

FIG. 1 shows a perspective view of a known rotary microtome 1 corresponding to the state of the art. On the base body of the microtome 2 a cutting movement is generated by a rotational driving movement at the handwheel 3. Thereby the stationary knife carrier with cutting knife 4 is passed vertically by the specimen holding device 5 with the thereto clamped specimen 6 to be thin cut. The specimen holding device being part of the vertical carriage 7. The feed unit 8, which is as well part of the vertical carriage, is thereby inducing in intervals the horizontal feed movements according to the double arrow 9. The vertical cutting movement is designated by the double arrow 10. To compensate the vertically acting mass of the vertical carriage 7 a compensation weight 11 is effective which is connected to the driving shaft 12 and therefore also to the handwheel 3. The driving shaft 12 is supported at the drive bearing 13 which is located at the base body 2 of the microtome. The vertical carriage 7 is guided preferably backlash-free by the inner and outer vertical guidance elements 14/14'.

Figure 2:
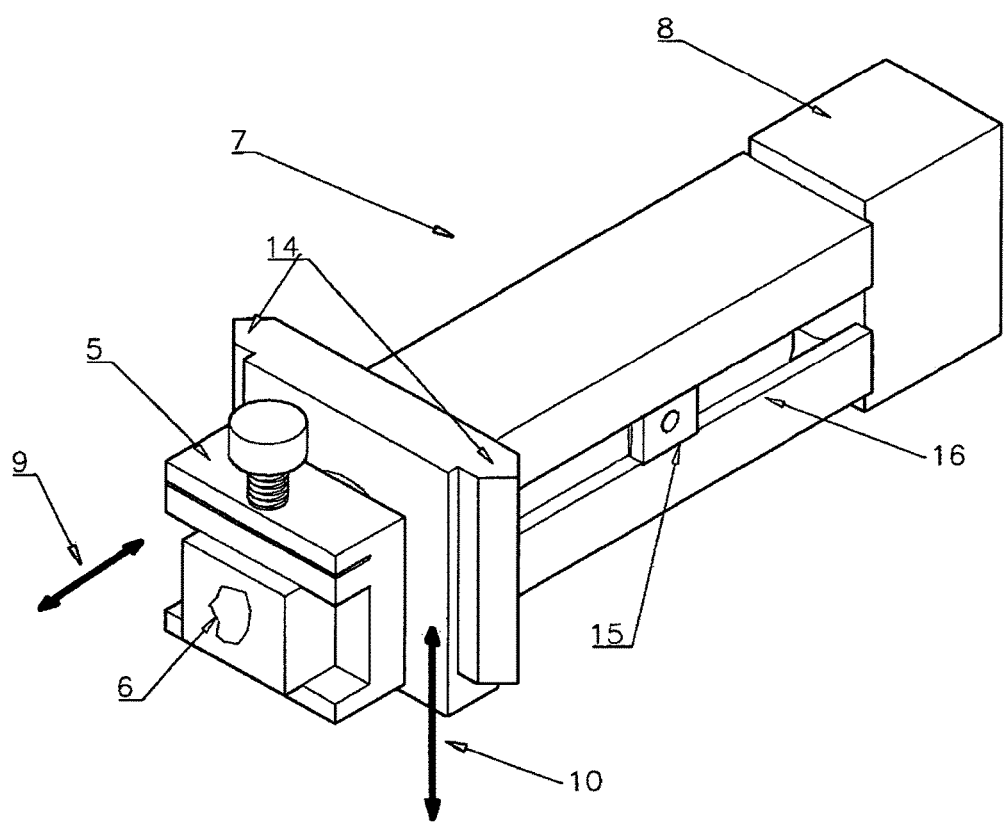

FIG. 2 shows a perspective view of a known vertical carriage according to the state of art. Herewith it is illustrated how the link block 15 is guided movable in the horizontally elongated slot-like link block guidance 16.

Figure 3:
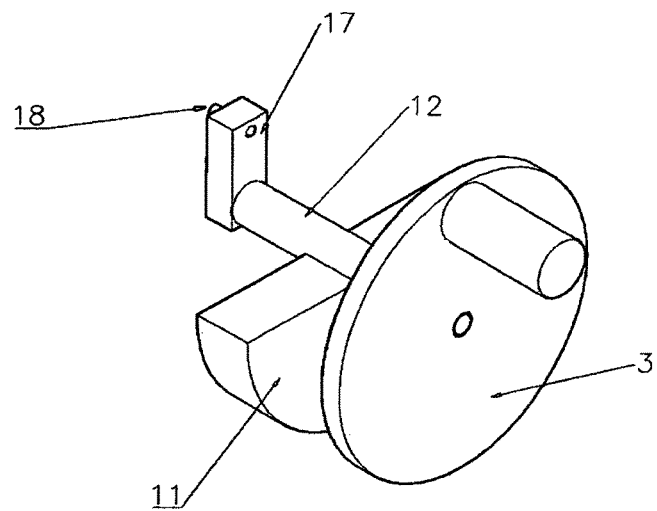

FIG. 3 shows a perspective view of a known driving unit according to the state of art. Here it is shown how the driving shaft 12 is connected to the crank arm 17 and the thereto connected crank pin 18.

Figure 4:
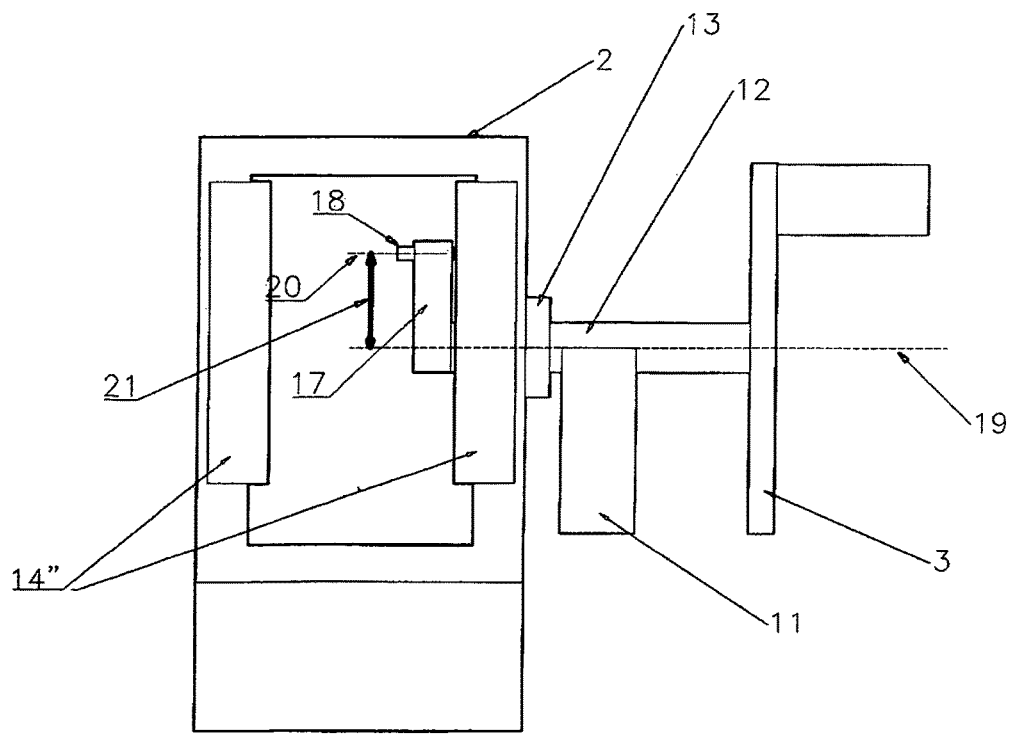

FIG. 4 shows a schematic depiction of a known rotary microtome with a cutting stroke adjustment according to the state of art. Herewith is the distance between driving axis 19 and centerline 20 of the crank pin adjustable. This is characterized by double-arrow 21. That way also the cutting stroke, which is corresponding twice the distance, is adjustable.

Figure 5:
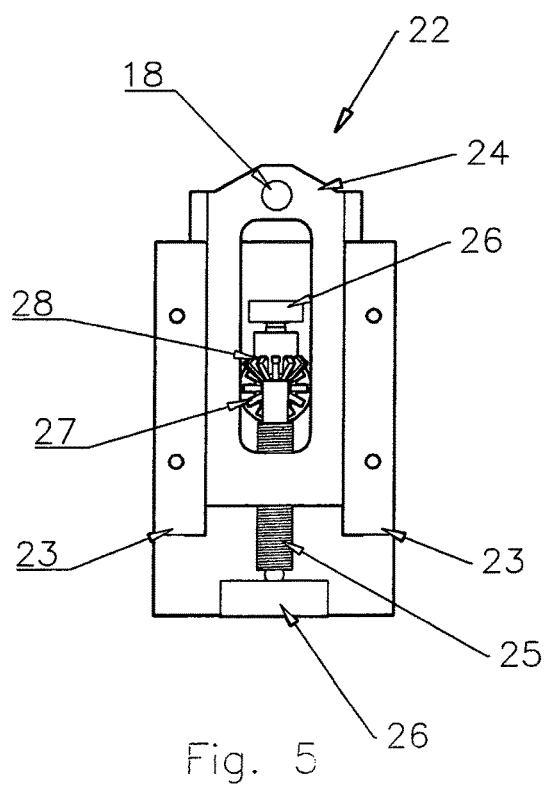

FIG. 5 shows the front view of a crank pin adjustment unit 22 according to the invention. The adjustment sledge 24 can be moved linear along a sledge guidance 23. The movement is caused at the nut thread of the adjustment sledge 24 by the adjustment spindle 25 which is supported rotatable in the step bearing 26. The adjustment spindle 25 itself is rotated by a bevel gear set which is consisting of a driving bevel gear wheel 27 and a down-force bevel gear wheel 28 which is connected to the adjustment spindle 25.

Figure 6:
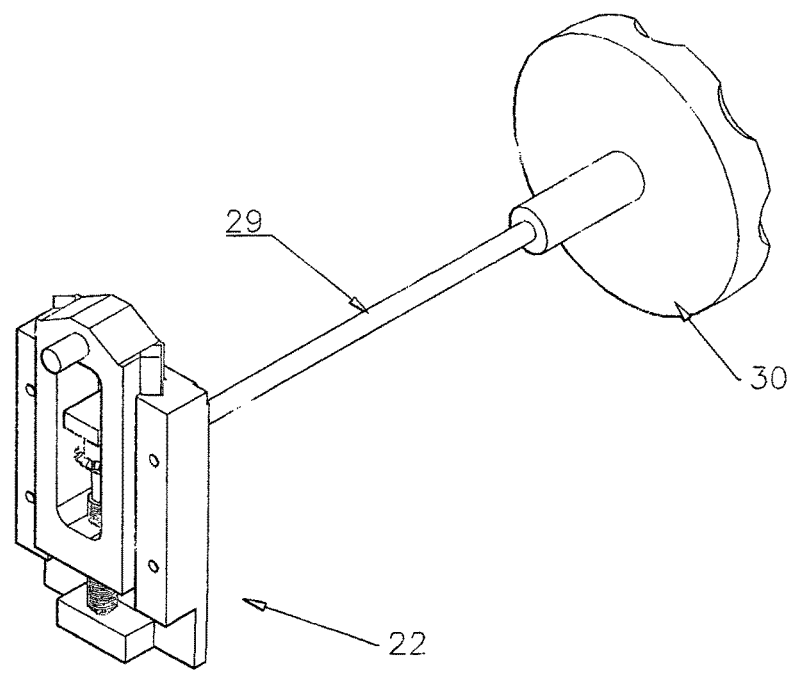

FIG. 6 shows a perspective view of the crank pin adjustment unit 22 with adjustment shaft 29 and a dial wheel 30 connected with it. The adjustment shaft 29 is thereby also connected to the driving bevel gear wheel 27, which is not visible here, but shown in FIG. 5

Figure 7:
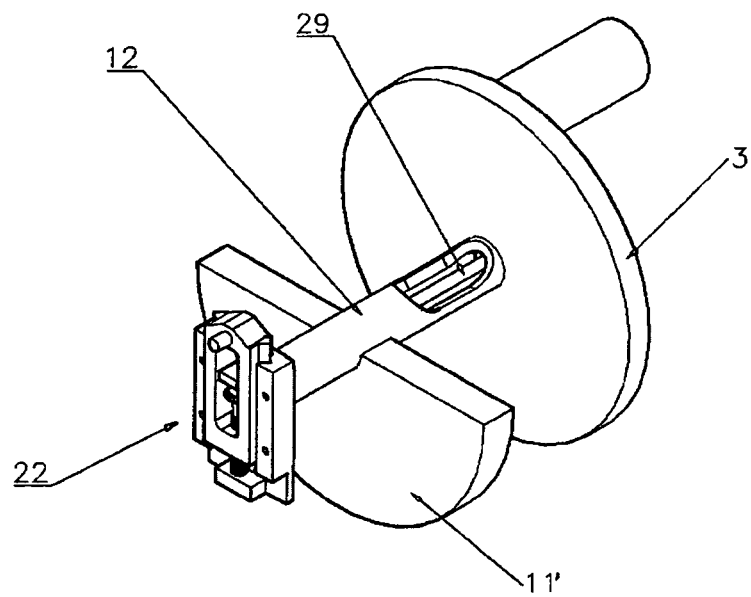

FIG. 7 shows a perspective view of a driving unit comprising a handwheel 3, a with it connected driving shaft 12, a thereto connected crank pin adjustment unit 22 and with a reduced counterweight 11' equally connected to the driving shaft 12. The counterweight 11' is calculated in its mass in away, that as described further down, an adjustment weight 31, which is not yet depicted here, leads to a total mass, which is necessary to fulfill the above-mentioned condition of equal moments of force $M_V=M_A$. The driving shaft 12 is illustrated here as broken open in order to make visible the inside located adjustment shaft 29 which is supported rotatable.

Figure 8:
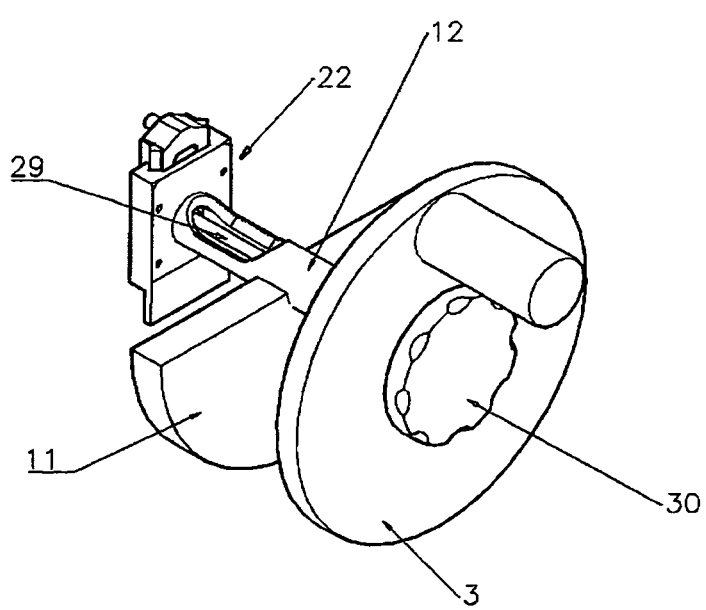

FIG. 8 shows a further perspective view of the driving unit with the same elements as already illustrated in FIG. 7. In addition there is only the dial wheel 30 visible which is arranged to be the control element.

FIG. 9 shows a perspective view of weight adjustment unit 34 on a handwheel 3 according to the invention. The adjustment weight 31 is illustrated, which is movable linear in direction of the double-arrow 33 via guiding grooves along the guidances 32 which are firmly connected to the handwheel 3. The elements of the weight adjustment unit 34 as depicted here are the worm gear 35, the matching worm gear wheel 36, which is connected to the transmission shaft 38 and herewith supported in the bearing brackets 37 which are connected to the handwheel 3. A rotary movement of the worm gear 35 is transferred to the push rod 40 via transmission shaft 38 which is firmly connected to the transmission lever 39, which is movable linked to the push rod 40 by the hinge 41. The push rod 40 itself is linked via supporting pin 42 to the adjustment weight 31, whereby this can be moved linearly according to double-arrow 33.

Figure 9A:
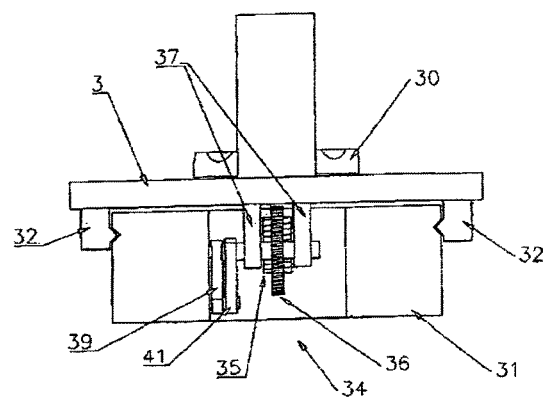

FIG. 9a shows a top view of the arrangement shown in FIG. 9. The guidances 32 are, in this example, connected to the handwheel 3. The adjustment weight 31 can move up and down via the guiding groves with respect to the fixed guidances 32.

FIG. 10 shows a perspective view of a coupled crank pin adjustment unit 22 with a weight adjustment unit 34 according to the invention. Thereby the driving shaft 12 is fixedly connected to the crank pin adjustment unit 22 and to the handwheel 3. The driving shaft 12 is depicted here widely opened in order to make visible the inside located and rotatable supported adjustment shaft 29 which is connected to the worm gear 35 shown in FIG. 9. In practice the driving shaft 12 has only a milled slot as wide as needed for a collision free meshing of worm gear wheel 36 and worm gear 35 depending on the respective dimensions of these elements in order to avoid an unnecessary weakening of the driving shaft 12. The adjustment shaft 29 is operated by the thereto connected dial wheel 30, which is not visible here.

FIG. 10a shows a perspective view similar to FIG. 9 and FIG. 10 with the difference that the guidances 32 of the weight adjustment unit 34 are directly connected to the driving shaft 12 which is differently formed in this example and which itself is connected to the handwheel 3.

Figure 10B:
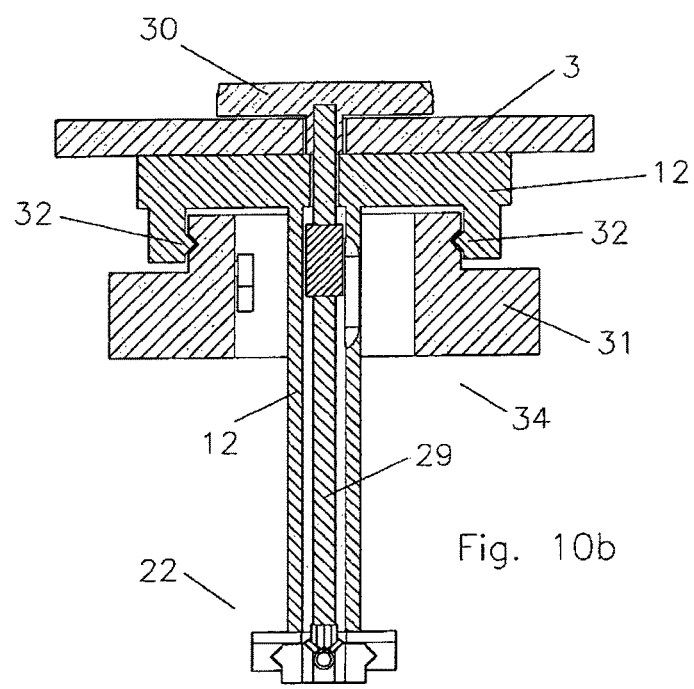

FIG. 10b shows a cross section of the arrangement in FIG. 10a along the axis of driving shaft 12. Hereby it is shown that, in this example, the guidances 32 are connected directly to the specially shaped driving shaft 12. The driving shaft 12 is connected to the handwheel 3. The dial wheel 30 is connected to the adjustment shaft 29 which is driving the weight adjustment unit 34 as well as the crank pin adjustment unit 22.

Figure 11:
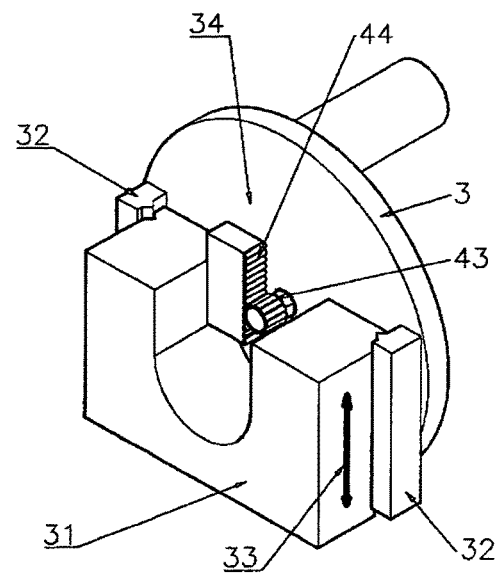

FIG. 11 shows a perspective view of a further example of a weight adjustment unit 34 according to the invention. It consists of a pinion 43, which is, analogous to the worm gear shown in FIG. 9, connected to the adjustment shaft 29 shown in FIG. 10 and a toothed rod 44 which is connected to the adjustment weight 31.

Figure 12:
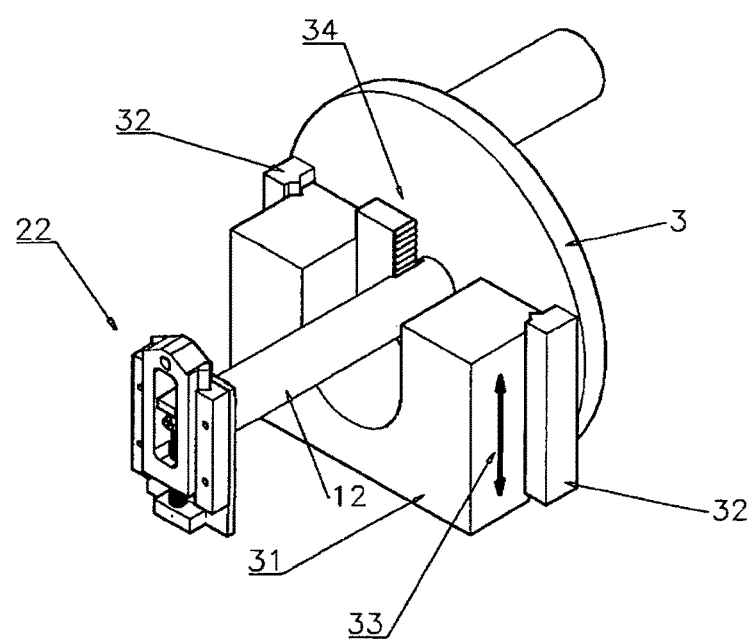

FIG. 12 shows a perspective view of a further example of a coupled crank pin adjustment unit 22 with a weight adjustment unit 34 consisting of a pinion 43 and a toothed rod 44 as shown in FIG. 11. Thereby the driving shaft 12 is fixedly connected to the crank pin adjustment unit 22 and to the handwheel 3. The driving shaft 12 is depicted here widely opened. As in the description of FIG. 10 it also applies here, that in a practical embodiment the driving shaft is milled out only as much as needed for a collision free meshing of pinion 43 and toothed rod 44.

Figure 13:
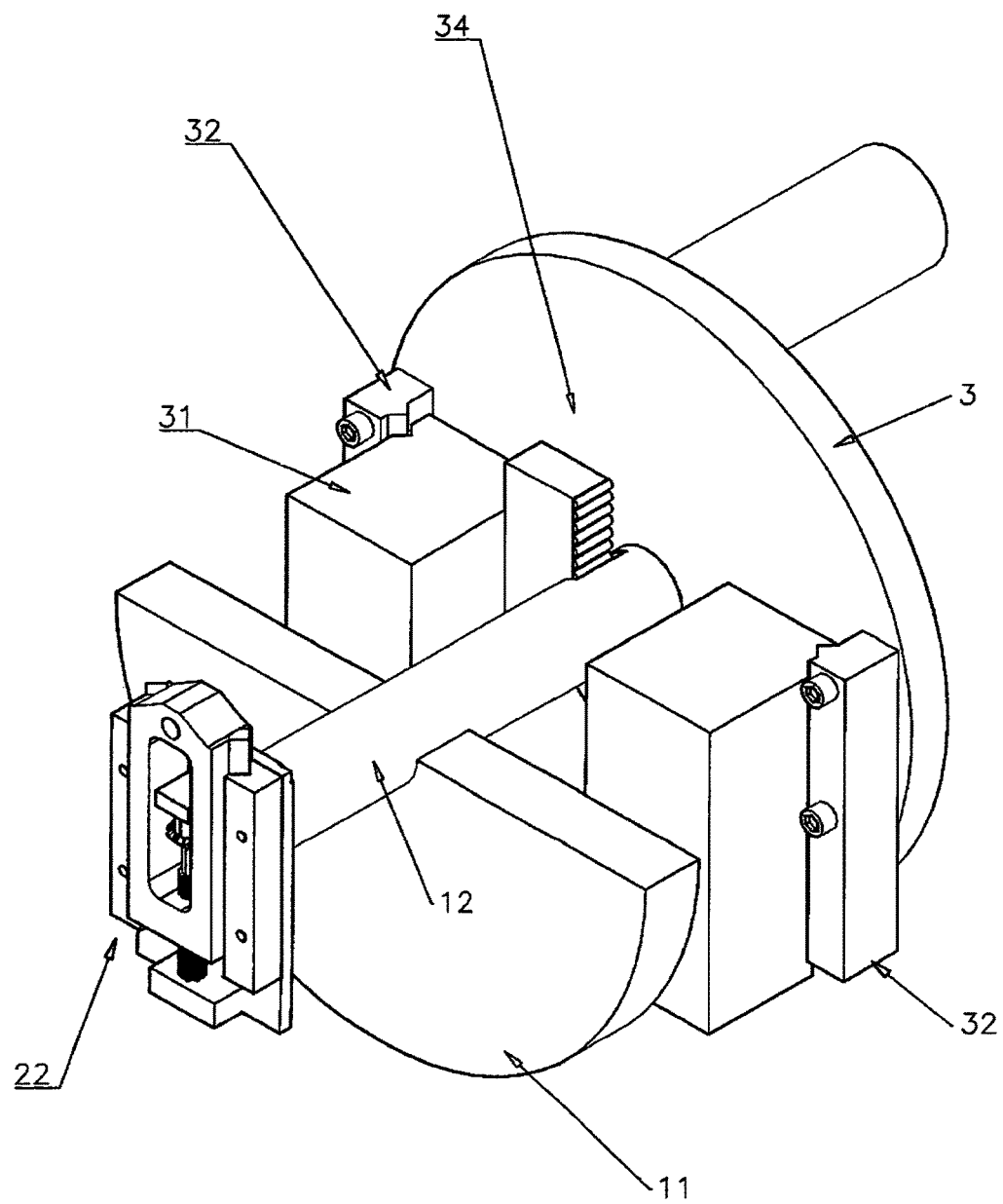

FIG. 13 shows a perspective view of a complete driving unit according to the invention with a coupled crank pin adjustment unit 22 and weight adjustment unit 34 together with a fixed counterweight 11', which is firmly connected to the driving shaft 12.

Figure 14:
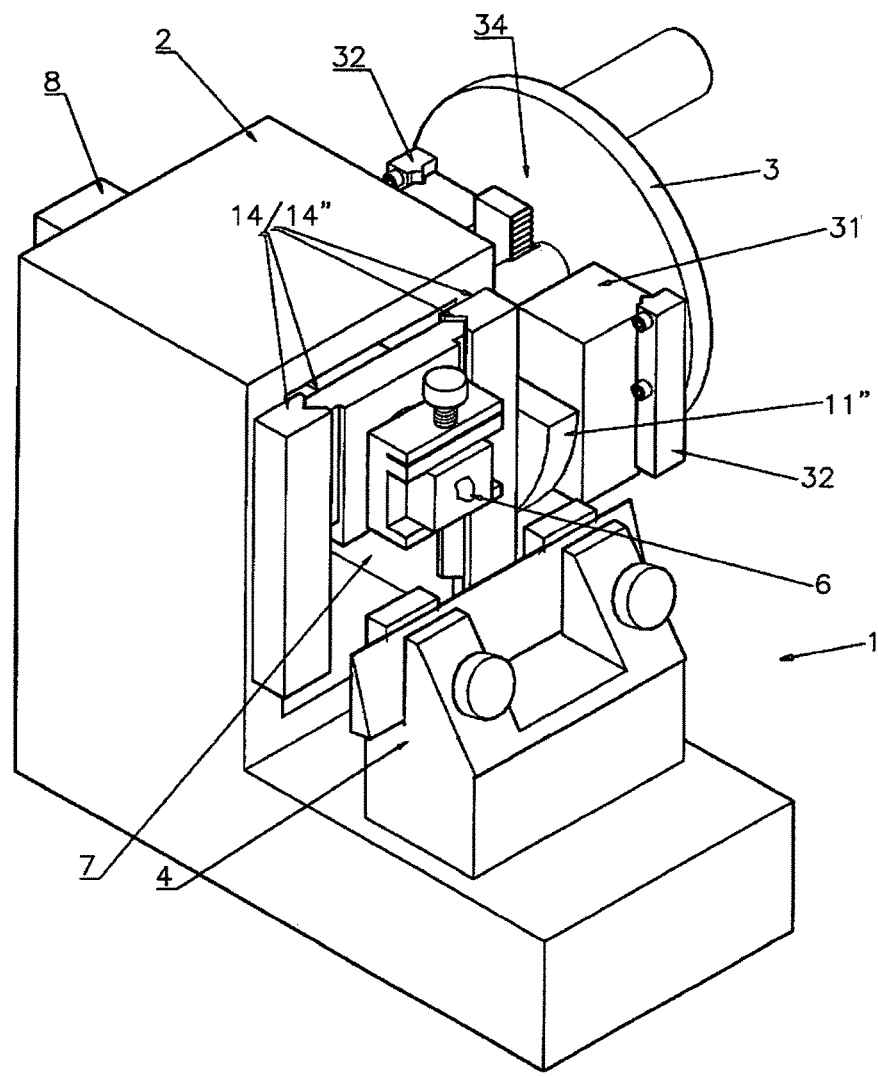

FIG. 14 shows a perspective view of an embodiment according to the invention of a rotary microtome 1 with a base body 2, a knife carrier with cutting knife 4, a specimen to be thin cut 6 and a vertical carriage 7 with feed unit 8, the vertical carriage 7 being guided by vertical guidance elements 14/14'. Attached to the handwheel 3 is the guidance 32 of the adjustment weight 31 which is supported slideable in it and which is activated via the weight adjustment unit 34. A partition of the fixed counterweight 11' is visible as well.

Figure 15:
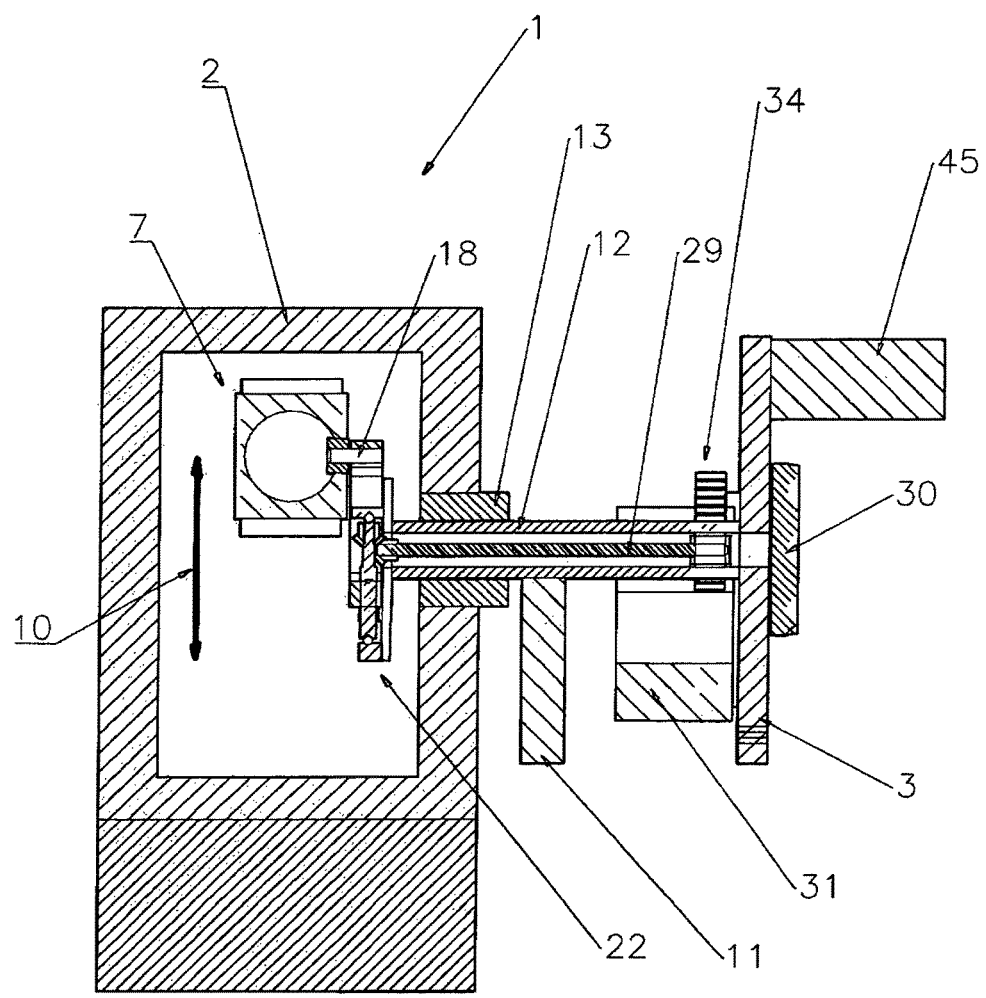

FIG. 15 shows a schematic depiction of a rotary microtome 1 with a coupled crank pin adjustment unit 22 and a weight adjustment unit 34 according to the invention. At the base body 2 of the microtome the drive bearing 13 is located in which the driving shaft 12 is rotatably supported. Fixedly connected to the driving shaft 12 is the body of the crank pin adjustment unit 22, the handwheel 3 with handle 45 and the invariant counterweight 11'. Inside the driving shaft 12, which is constructed as hollow shaft, the adjustment shaft 29 is supported rotatably and concentrically. The adjustment shaft 29 is fixedly connected with the dial wheel 30 as well as with the driving adjustment means of the crank pin adjustment unit 22 and the weight adjustment unit 34. An operation of the dial wheel 30 which acts as operating element accomplishes simultaneously an adjustment of the crank pin adjustment unit 22 by adjusting the effective distance of the crank pin 18 and herewith the cutting stroke length as well as an adjustment of the adjustment weight 31 induced by the weight adjustment unit 34. Thereby the moment of force which is generated by the vertical carriage 7 at the lever arm of the crank pin 18 is compensated by an equal but opposite moment of force which is generated by the invariant counterweight 11' and the adjustment weight 31 with their respective effectual lever arms.

Figure 16:
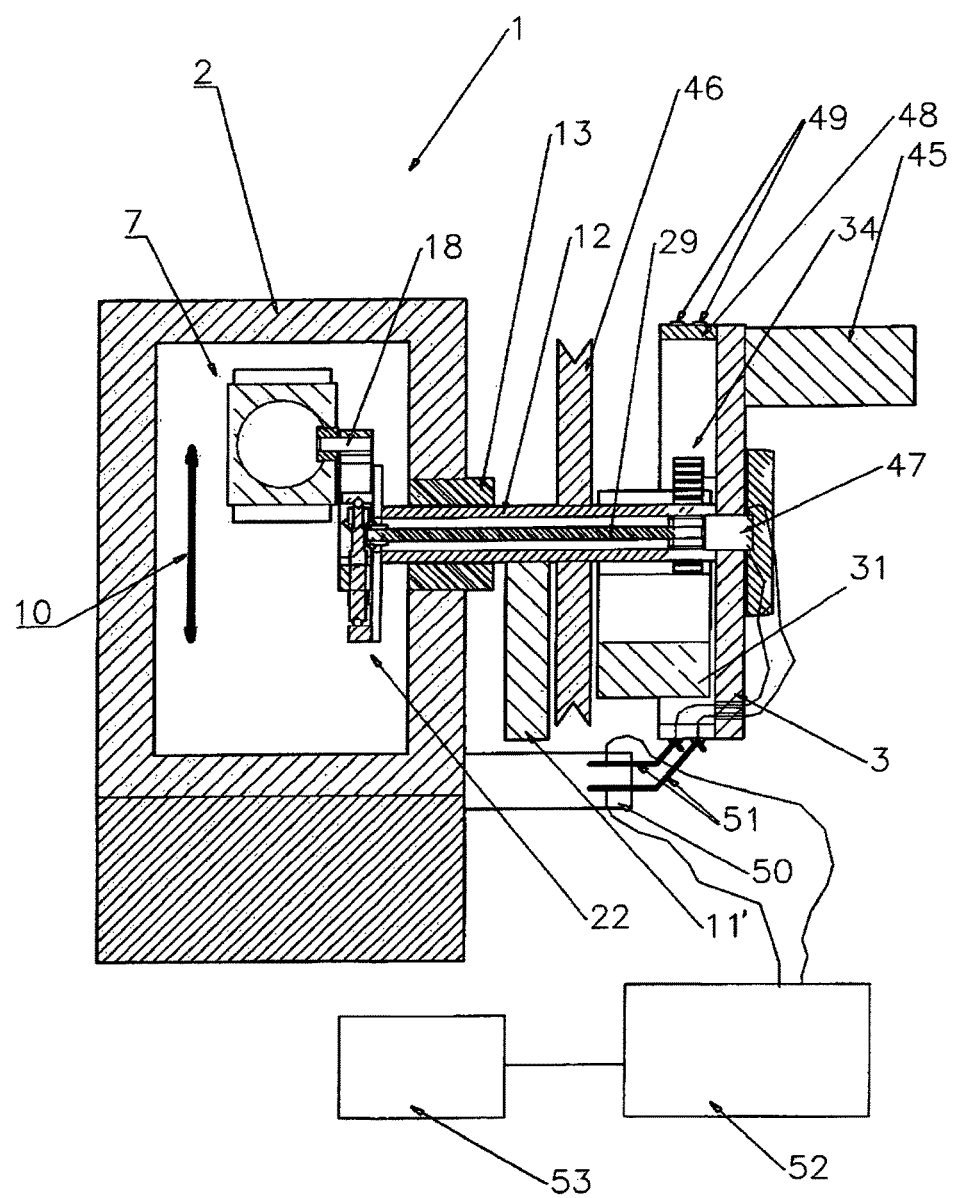

FIG. 16 shows a schematic view of a rotary microtome 1. In difference to FIG. 15 there is shown additionally a pulley 46 which is connected to the driving shaft 12 and which enables in addition to the drive with the handwheel 3 also a motorized drive of the cutting movement by a connection to a driving motor, which is not shown here in this figure. Furthermore it is shown here an electrically working actuator in form of a gear motor 47 which is connected with the adjustment shaft 29 instead of the dial wheel 30 shown in FIG. 15 and which therefore generates the adjustment movement for the crank pin adjustment unit 22 and the weight adjustment unit 34. The gear motor 47 is fixedly mounted with its housing to the inside of the driving shaft 12 and is connected via electrical wiring with the slip rings 49, which are mounted to the electrically isolated ring 48 which is bonded to the handwheel 3. The slip rings 49 are connected electrically with the spring contacts 51 which are fastened to an isolated body 50 which is joined to the microtome base body 2. The spring contacts 51 are electrically connected with a control unit 52, here shown as part of a block diagram, which supplies the gear motor 47 with electrical power and which is itself triggered by an operation unit 53, which is shown as part of a block diagram as well.

LIST OF COMPONENT PARTS

1 Rotary microtome
2 Microtome base body
3 Handwheel
4 Knife carrier with cutting knife
5 Specimen holding device
6 Specimen
7 Vertical carriage
8 Feed unit
9 Horizontal feed movement
10 Vertical cutting movement
11/11' Counterweight
12 Driving shaft
13 Drive bearing
14 14/14' Vertical guidance elements
15 Link block
16 Link block guidance
17 Crank arm
18 Crank pin
19 Drive axis
20 Crank pin centerline
21 Distance drive axis to creak pin centerline
22 Crank pin adjustment unit
23 Sledge guidance
24 Adjustment sledge
25 Adjustment spindle
26 Step bearing
27 Driving bevel gear wheel
28 Down-force bevel gear wheel
29 Adjustment shaft
30 Dial wheel
31 Adjustment weight
32 Guidance for adjustment weight
33 Direction of weight adjustment
34 Weight adjustment unit
35 Worm gear
36 Worm gear wheel
37 Bearing brackets
38 Transmission shaft
39 Transmission lever
40 Push rod
41 Hinge
42 Supporting pin
43 Pinion
44 Toothed rod
45 Handle
46 Pulley
47 Gear motor
48 Isolated ring
49 Slip rings
50 Isolated body
51 Spring contacts
52 Control unit
53 Operational unit

The invention claimed is:

1. A rotary microtome (1) with a vertical carriage (7) performing a cutting stroke, a driving shaft (12) for generating a vertical cutting movement (10), a cutting stroke adjustment unit of the cutting stroke and with a counterweight (11') and an adjustment weight (31) with an adjustable compensation mass, the microtome comprising, that the driving shaft (12) is formed as a hollow shaft which has an opening on a lateral surface area of said hollow shaft, that a crank pin adjustment unit (22) is connected on an output side of the driving shaft (12), which is forming with an adjustable crank pin a crank arm of a circular driving movement, that a control element (30) is located opposed to the output side of the driving shaft (12) in extension of the driving shaft (12), that a weight adjustment unit (34) is placed on a segment between two shaft ends of the driving shaft (12), whereby a guidance (32) of the adjustment weight (31) is connected directly to the driving shaft (12) or indirectly via the handwheel (3), that the control element (30) activates translational or rotatory acting adjustment means, which are located inside the driving shaft (12) and which drive simultaneously in a single operation the crank pin adjustment unit (22) as well as the weight adjustment unit (34), which is driven thru the opening in the lateral surface of the driving shaft (12) by the inside located adjustment means (29), providing that a moment of force, which is generated from the weight of the vertical carriage (7) at a crank pin (18) multiplied with a lever arm between a medial axis of the driving shaft (12) and a medial axis of the crank pin (18), will be compensated for any angle of the circular driving motion of the driving shaft (12) by an algebraic sum of partial moments of force generated from the counterweight (11') and the adjustment weight (31) multiplied with their respective lever arms from their centers of mass to the medial axis of the driving shaft (12).

2. A rotary microtome (1) with a vertical carriage (7) performing a cutting stroke, a driving shaft (12) for generating a vertical cutting movement (10), a cutting stroke adjustment unit of the cutting stroke and with a counterweight (11') and an adjustment weight (31) with an adjustable compensation mass, the microtome comprising, that the driving shaft (12) is formed as a hollow shaft which has an opening on a lateral surface area of said hollow shaft, that a crank pin adjustment unit (22) is connected on an output side of the driving shaft (12), which is forming with an adjustable crank pin a crank arm of a circular driving movement, that an electrically powered actuator (47) is located inside of the driving shaft (12) which is mounted with its housing fixedly to the inside of the driving shaft (12) and which is supplied electrically via slider contacts (49) on the driving shaft (12) or the handwheel (3) and the actuator (47) being actuated by a control unit (52) which itself is triggered by an operational command to an operational unit (53), that a weight adjustment unit (34) is placed on a segment between two shaft ends of the driving shaft (12), whereby a guidance (32) of the adjustment weight (31) is connected directly to the driving shaft (12) or indirectly via the handwheel (3), that the actuator (47) activates translational or rotatory acting adjustment means (29), which are located inside the driving shaft (12) and which drive simultaneously at a single command the crank pin adjustment unit (22) as well as the weight adjustment unit (34), which is driven thru the opening in the lateral surface of the driving shaft (12) by the inside located adjustment means (29), providing that a moment of force, which is generated from the weight of the vertical carriage (7) at a crank pin (18) multiplied with a lever arm between a medial axis of the driving shaft (12) and a medial axis of the crank pin (18), will be compensated for any angle of the circular driving motion of the driving shaft (12) by an algebraic sum of partial moments of force generated from the counterweight (11') and the adjustment weight (31) multiplied with their respective lever arms from their centers of mass to the medial axis of the driving shaft (12).

3. A rotary microtome according to claim 1, wherein the partial moment of force which is generated from the adjustment weight (31) multiplied with the lever arm of its center of mass to the medial axis of the driving shaft (12) can be a positive as well as a negative magnitude in relation to a total magnitude of the moment of force to be composed from the partial moments of force for compensation of the moment of force, which is generated from the weight of the vertical carriage (7) at the crank pin (18) multiplied with the lever arm between the medial axis of the driving shaft (12) and medial axis of the crank pin (21).

4. A rotary microtome according to claim 2, wherein the partial moment of force which is generated from the adjustment weight (31) multiplied with the lever arm of its center of mass to the medial axis of the driving shaft (12) can be a positive as well as a negative magnitude in relation to a total magnitude of the moment of force to be composed from the partial moments of force for compensation of the moment of force, which is generated from the weight of the vertical carriage (7) at the crank pin (18) multiplied with the lever arm between the medial axis of the driving shaft (12) and medial axis of the crank pin (21).

5. A rotary microtome according to claim 1, wherein the control element is a dial wheel (30) and where said rotational adjustment means is the adjustment shaft (29) which is supported concentrically inside the driving shaft (12) and which is fixedly connected to the dial wheel (30) and to further rotatory acting adjustment means for driving the crank pin adjustment unit (22) and the weight adjustment unit (34).

6. A rotary microtome according to claim 3, wherein the control element is a dial wheel (30) and where said rotational adjustment means is the adjustment shaft (29) which is supported concentrically inside the driving shaft (12) and which is fixedly connected to the dial wheel (30) and to further rotatory acting adjustment means for driving the crank pin adjustment unit (22) and the weight adjustment unit (34).

7. A rotary microtome according to claim 2, wherein said actuator is a gear motor (47) and where said rotational adjustment means is the adjustment shaft (29) which is supported concentrically inside the driving shaft (12) and which is fixedly connected to the driving shaft of the gear motor (47) and to further rotatory acting adjustment means for driving the crank pin adjustment unit (22) and the weight adjustment unit (34).

8. A rotary microtome according to claim 4, wherein said actuator is a gear motor (47) and where said rotational adjustment means is the adjustment shaft (29) which is supported concentrically inside the driving shaft (12) and which is fixedly connected to the driving shaft of the gear motor (47) and to further rotatory acting adjustment means for driving the crank pin adjustment unit (22) and the weight adjustment unit (34).

9. A rotary microtome according to claim 5, wherein said further rotatory adjustment means are pinions, worm gears or bevel gears.

10. A rotary microtome according to claim 8, wherein said further rotatory adjustment means are pinions, worm gears or bevel gears.

11. A rotary microtome according to one of the claim 1, 2, or 3 10, wherein the crank pin adjustment unit (22) is actuated by the adjustment shaft (29) with a drive bevel gear wheel (27).

12. A rotary microtome according to one of the claim 1, 2 or 3 10, wherein the weight adjustment unit (34) is actuated by the adjustment shaft (29) with a worm gear (35).

13. A rotary microtome according to one of the claim 1, 2 or 3 10, wherein the weight adjustment unit (34) is actuated by the adjustment shaft (29) with a pinion (43).

14. A rotary microtome according to claim 11, wherein the crank pin adjustment unit (22) is composed of a sledge guidance (23) and an adjustment sledge (24) to which the crank pin is fastened and which can be shifted via a nut thread when an adjustment spindle (25) is turned, whereby the adjustment spindle is supported in two step bearings (26) which are fixed to the body of the sledge guidance and whereby a down-force bevel gear wheel (28) is connected to the adjustment spindle (25) which is meshing with the drive bevel gear wheel (27).

15. A rotary microtome according to claim 12, wherein the weight adjustment unit (34) is composed of:
 a push rod (40), which is shifting the adjustment weight (31) in the guidance of adjustment weight (32),
 a transmission lever (39),
 a transmission shaft (38), which is supported in bearing brackets (37)
 a worm gear wheel (36) connected to the transmission shaft (38), which is meshing with the worm gear (35) thru the opening in the lateral surface of the driving shaft (12).

16. A rotary microtome according to claim 13, wherein the weight adjustment unit (34) is composed of a toothed rod (44), which is connected to the adjustment weight (31) and which is meshing thru the opening of the lateral surface of the driving shaft (12) with the pinion (43).

17. A rotary microtome according to claim 6, wherein said further rotatory adjustment means are pinions, worm gears or bevel gears.

18. A rotary microtome according to claim 7, wherein said further rotatory adjustment means are pinions, worm gears or bevel gears.

* * * * *